United States Patent
Krook et al.

(10) Patent No.: US 9,902,551 B2
(45) Date of Patent: Feb. 27, 2018

(54) DISPENSER AND METHOD OF DISPENSING

(75) Inventors: Fredrik Krook, Mölndal (SE); Shadi Ståhl, Göteborg (SE); Kent Hermansson, Göteborg (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 108 days.

(21) Appl. No.: 14/411,118

(22) PCT Filed: Jun. 28, 2012

(86) PCT No.: PCT/SE2012/050733
§ 371 (c)(1),
(2), (4) Date: Dec. 24, 2014

(87) PCT Pub. No.: WO2014/003617
PCT Pub. Date: Jan. 3, 2014

(65) Prior Publication Data
US 2015/0314945 A1    Nov. 5, 2015

(51) Int. Cl.
*B65D 83/08* (2006.01)
*A44B 18/00* (2006.01)
(Continued)

(52) U.S. Cl.
CPC .......... *B65D 83/0841* (2013.01); *A44B 18/00* (2013.01); *A44B 18/0023* (2013.01);
(Continued)

(58) Field of Classification Search
CPC ............ B65D 83/0841; B65D 83/0835; B65D 85/672; A44B 18/00; A44B 18/0023; A61F 13/66; A61F 13/64; A61F 15/001
(Continued)

(56) References Cited

U.S. PATENT DOCUMENTS 2,848,104 A * 8/1958 Schor ................... B65D 85/672
                                                        206/391
2,861,753 A * 11/1958 Sipior ................ B65D 83/0841
                                                        206/408
(Continued)

FOREIGN PATENT DOCUMENTS

EP    0122981 A2    10/1984
FR    2830726 A1    4/2003
(Continued)

OTHER PUBLICATIONS

English-language translation of a Russian Decision of Grant dated Mar. 11, 2016 issued in corresponding Russian application No. 2015102607 (6 pages).

*Primary Examiner* — Sameh Tawfik
(74) *Attorney, Agent, or Firm* — Drinker Biddle & Reath LLP

(57) ABSTRACT

A dispenser for on-demand dispensing of a length of belt material and a first hook material patch is provided. The dispenser includes a first holder for a roll or a stack of continuous belt material, a dispensing outlet for the belt material, a separating element for separating the length of belt material from the roll or the stack of continuous belt material, a second holder for at least the first hook material patch, and a hook material patch providing device. The hook material patch providing device is arranged to cooperate with the second holder to dispense the first hook material patch. There is further provided a method of on-demand dispensing a belt.

6 Claims, 4 Drawing Sheets

(51) Int. Cl.
  *A61F 13/64* (2006.01)
  *A61F 13/66* (2006.01)
  *A61F 15/00* (2006.01)
  *B65D 85/672* (2006.01)

(52) U.S. Cl.
  CPC .............. *A61F 13/64* (2013.01); *A61F 13/66* (2013.01); *A61F 15/001* (2013.01); *B65D 83/0835* (2013.01); *B65D 85/672* (2013.01)

(58) Field of Classification Search
  USPC .......................................................... 493/37
  See application file for complete search history.

(56) References Cited

U.S. PATENT DOCUMENTS

| | | | | |
|---|---|---|---|---|
| 3,150,807 | A * | 9/1964 | Loughary | A47F 7/17 225/47 |
| 3,302,781 | A * | 2/1967 | Rudnick | B65D 85/67 206/391 |
| 3,660,958 | A * | 5/1972 | Garrison | B65D 85/672 206/410 |
| 4,027,795 | A * | 6/1977 | Rigden | B41J 11/58 206/409 |
| 4,531,634 | A * | 7/1985 | Jung-Chi | A44B 18/00 206/346 |
| 4,546,879 | A * | 10/1985 | Viscasillas | B65D 75/16 206/391 |
| 4,723,723 | A | 2/1988 | Asahi et al. | |
| 4,807,753 | A * | 2/1989 | Goldstein | A61F 15/002 206/390 |
| 4,964,860 | A | 10/1990 | Gipson et al. | |
| 4,973,326 | A | 11/1990 | Wood et al. | |
| 4,994,054 | A | 2/1991 | Pigneul et al. | |
| 5,135,522 | A | 8/1992 | Fahrenkrug et al. | |
| 5,906,604 | A | 5/1999 | Rönnberg et al. | |
| 5,971,970 | A | 10/1999 | Carlbark et al. | |
| 2003/0226868 | A1 * | 12/2003 | Monden | B65D 83/0841 225/39 |
| 2010/0319167 | A1 | 12/2010 | Nirmel | |

FOREIGN PATENT DOCUMENTS

| | | |
|---|---|---|
| GB | 989872 A | 4/1965 |
| GB | 2277865 A | 11/1994 |
| GB | 2277866 A | 11/1994 |
| JP | 2006-325939 A | 12/2006 |
| WO | WO 90/01286 A1 | 2/1990 |

* cited by examiner

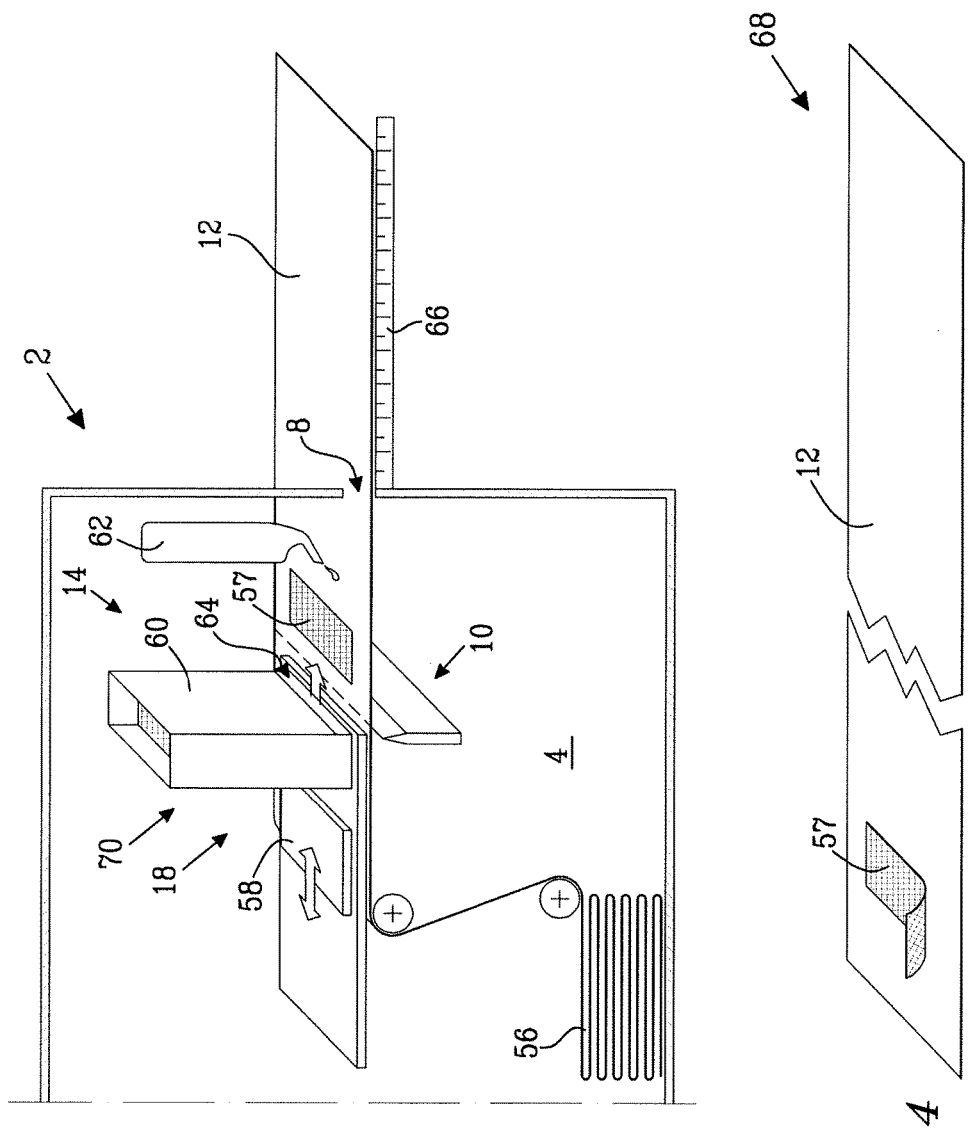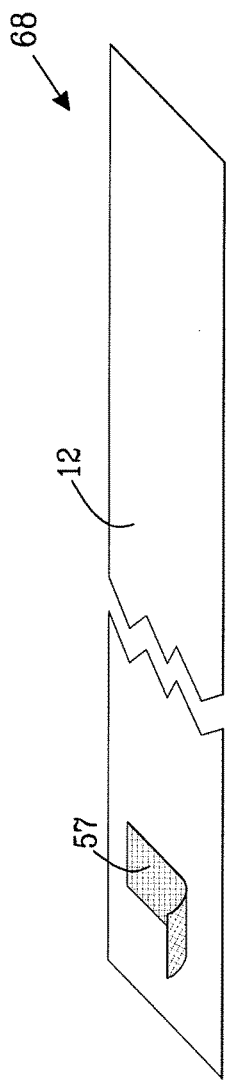

DISPENSER AND METHOD OF DISPENSING

CROSS-REFERENCE TO PRIOR APPLICATION

This application is a § 371 National Stage Application of PCT International Application No. PCT/SE2012/050733 filed Jun. 28, 2012, which is incorporated herein in its entirety.

TECHNICAL FIELD

The present disclosure relates to a dispenser for dispensing a belt. The disclosure also relates to a method of dispensing a belt.

BACKGROUND

Absorbent products such as products used for incontinence care are in some embodiments held up by a belt. Such belts are for instance known from GB 2277865 and GB 2277866. These belts are held around a waist of a user by attachment means comprising of flexible strip of hook elements engaging with the belt material. Thus, a releasable hook and loop fastening arrangement is provided. The belt may be reused and does not have to be exchanged with every change of absorbent product.

Double sided hook patches are known as such, e.g. from FR 2830726, US 2010/0319167, and JP 2006325939. FR 2830726 discloses the use of a hook patch having a different number of hooks on each of its two different sides to achieve different attachment properties. The use of hook patches is disclosed in connection with various garments, including belts. US 2010/0319167 discloses a hook and loop fastening system comprising a double sided hook patch, the hook patch having different attachment properties on its two sides thanks to differently large areas of hooks on the two sides of the hook patch. The purpose of the system is to permit the hook patch to be removed prior to washing a relevant textile. JP 2006325939 discloses a double sided hook patch to be used in connection with diaper covers, clothes, and linen. The purpose of the double sided hook patch again, is to permit removal of the hook patch prior to washing a relevant textile.

Today, in connection with absorbent products, commonly one or more disposable belts are provided together with every package of absorbent products for incontinence care. Thus, too many or too few belts may be provided for a particular user of absorbent products or for a particular group of users of absorbent products. Furthermore, users of absorbent products have different waist-measurements, which should be respected in order to satisfy customers, preferably without wasting belt material.

SUMMARY

It is desired to provide users of absorbent products with a means and a method of efficient and economical consumption of disposable belts for holding up such absorbent products.

Disclosed herein is a dispenser for on-demand dispensing of a length of belt material and a first hook material patch. The length of belt material and the first hook material patch are adapted for use with an absorbent product. The dispenser includes a first holder for a roll or a stack of continuous belt material, a dispensing outlet for the belt material, a separating element for separating the length of belt material from the roll or the stack of continuous belt material, a second holder for at least the first hook material patch, and a hook material patch providing device. The hook material patch providing device is arranged to cooperate with the second holder for dispensing the first hook material patch.

Since the dispenser includes separate holders for belt material and hook material, a separating element, and a hook material patch providing device, a user is permitted to dispense a belt for use with an absorbent product from the dispenser, when such a belt is required. There is neither a waste of belts nor a shortage of belts for use with absorbent products. Furthermore, each belt may be dispensed at a length corresponding to the particular use, which reduces waste of belt material.

The dispenser may be a stand-alone unit or it may be a wall mounted unit. The dispenser may be used at home, in a hospital, or other care institution. The absorbent product may be a product used for incontinence care. Separating of the belt material from the roll or stack of continuous belt material may take place before, or after, depositing the first hook material patch onto the length of belt material. The dispenser may be adapted for use with non-perforated belt material, in which case the separating element may be adapted for cutting the belt material. Alternatively, the dispenser may be adapted for use with perforated belt material, in which case the separating element may include a nip or a serrated edge against which a perforation may be torn. Herein, the terms—hook material, and hook surface structure—are to be interpreted to encompass the hook part of a hook and loop fastening system, e.g. known as a VELCRO® system. As such the "hooks" may have many different shapes which are adapted to engage with a loop part of the hook and loop fastening system. Examples of the different shapes include a J-shape, mushroom shape, and palm tree shape.

According to embodiments, the length of belt material may be separately dispensed from the dispenser. The first hook material patch may be separately dispensed from the dispenser. That is, the length of belt material and the first hook material patch may be dispensed separately from each other from the dispenser. In this manner a user may dispense e.g. a length of belt material to form a belt for an absorbent product together with a hook material patch previously used with another belt.

According to embodiments, the dispenser may be adapted to dispense one length of belt material at a time. A length of belt material dispensed through the dispensing outlet has a belt width. The first holder may be adapted to hold a roll or a stack of continuous belt material having a width corresponding to the belt width. In this manner, the dispenser may be adapted for dispensing each length of belt material just prior to its use as a belt by an end user of the belt and a related absorbent product.

According to embodiments, the hook material patch providing device may include a cutting element for separating the first hook material patch from a roll or a stack of the continuous web of hook material held in the second holder, or the hook material patch providing device may include a feeding member for feeding the first hook material patch from a stack of pre-cut material patches held in the second holder. In this manner, the first hook material patch may be deposited onto the length of belt material. Alternatively, the first hook material patch, as such, may be dispensed from the dispenser to a user.

According to embodiments, the dispenser may include a depositing arrangement arranged for depositing the first hook material patch onto the length of belt material for on-demand dispensing of a belt for use with an absorbent product. The hook material patch providing device may include the depositing arrangement. In this manner a belt ready for use with a related absorbent product may be provided directly from the dispenser. Separating the belt material from the roll or stack of continuous belt material may take place before, or after, depositing the first hook material patch onto the length of belt material.

A belt dispensed from the dispenser may be a disposable belt. The term—disposable belt—is to be interpreted to mean that such a belt is only usable for its intended purpose for a limited period of time, during which period it will become worn out. Such a limited period may be e.g. less than a week of use. In contrast, an ordinary belt, such as a belt used with garments e.g. pants, may be used over a much longer period of time before it becomes worn out, often over many years. The belt is a unit separate from the absorbent product with which it is to be used. As such, the belt may be attached around a waist region of a user independently of a related absorbent product. Thus, the belt may be used with a number of absorbent products, one after the other. An absorbent product to be used in conjunction with the belt may be attachable to the belt. The absorbent product may be attached to the belt using hook material patches attached to the absorbent product. The belt may be substantially flat and may be flexible such that it may be slung around the waist region of a user.

According to embodiments, the dispenser may be adapted to dispense any of: a length of belt material, a first hook material patch, and a belt including a length of belt material and a thereto attached first hook material patch.

According to embodiments, the second holder may be adapted to hold a roll or a stack of a continuous web of hook material and the depositing arrangement may include the cutting element for separating the first hook material patch from the roll or the stack of the continuous web of hook material. The dispenser may include a feeding arrangement for feeding the continuous web of hook material in a direction from the second holder towards the cutting element. In this manner, the dispenser may be filled with a web of hook material, from which the first hook material patch may be separated to be deposited onto the length of belt material. The term "stack of continuous web of hook material," is to be interpreted to encompass either a single piece of continuous web of hook material folded up to form a stack, or several pieces of continuous web of hook material stacked upon each other. In both cases, the single piece as well as each of the several pieces has a length corresponding to the length of at least two hook material patches.

According to embodiments, the second holder may be adapted to hold a stack of pre-cut hook material patches. The stack of pre-cut hook material patches may include the first hook material patch. The depositing arrangement may include the feeding member arranged to feed the first hook material patch onto the length of belt material.

According to embodiments, the dispenser may be adapted for use with a belt material having a loop surface structure. In this manner, in use of the dispensed belt around a waist of a user of a related absorbent product, the first hook material patch may interconnect directly with the dispensed belt.

Herein, the term—loop surface structure—is to be understood to encompass a surface structure to which a hook material of a hook and loop fastening system is attachable. Accordingly, a loop surface structure may include fibers or threads, extending from a surface and back into the surface to define genuine loops, as well as a surface structure including fibers or threads extending out from a surface and having loose ends, which fibers or threads entangle with each other.

According to embodiments, the hook material of the first hook material patch has two sides, each of the two sides may be provided with a hook surface structure. In this manner, a first side of the first hook material patch may engage with the length of belt material when being deposited thereon, to thereby form the belt. The dispensed belt may thereafter be attached around a waist of a user of a related absorbent product by means of the second side of the first hook material patch interconnecting with the dispensed belt.

According to embodiments, the dispenser may include a first compartment including the first holder and a second compartment including the second holder. The first compartment and the second compartment may be separately openable for replenishing the dispenser with continuous belt material and hook material. In this manner, the continuous belt material and hook material may be separately replenished. According to embodiments, the first holder may form a portion of the first compartment, or the first holder may form substantially the entire first compartment. According to embodiments, the second holder may form a portion of the second compartment, or the second holder may form substantially the entire second compartment.

According to embodiments, the dispenser may include a measuring device arranged for measuring the length of belt material. In this manner, a user may easily dispense a belt of a particular length. The measuring device may be e.g. a measuring-tape, a ruler, or a counter being affected by the belt material as it is dispensed. The measuring device may be mechanical or electronic.

Also disclosed herein is a method of on-demand dispensing a belt for use with an absorbent product, the dispenser including a first holder holding a roll or a stack of continuous belt material, a dispensing outlet for the belt material, a separating element for separating a length of belt material from the roll or the stack of continuous belt material, a second holder holding at least a first hook material patch, and a depositing arrangement arranged for depositing the first hook material patch onto the length of belt material. The method includes:

extracting a length of belt material from the roll or the stack of continuous belt material via the dispensing outlet, depositing the first hook material patch onto the length of belt material utilizing the depositing arrangement, and separating the length of belt material from the roll or stack of continuous belt material to thereby form the belt.

Further features of, and advantages with, the present invention will become apparent when studying the appended claims and the following detailed description. Those skilled in the art will realize that different features of the present invention may be combined to create embodiments other than those described in the following, without departing from the scope of the present invention, as defined by the appended claims.

BRIEF DESCRIPTION OF THE DRAWINGS

Various aspects and embodiments of the invention, including particular features and advantages, will be readily understood from the following detailed description and the accompanying drawings, in which:

FIG. 3 illustrates a partial cross section through yet another dispenser according to some embodiments, FIG. 4 illustrates a belt according to some embodiments, the belt being adapted for use with an absorbent product.

DETAILED DESCRIPTION OF PARTICULAR EMBODIMENTS

Certain embodiments of the present invention will now be described more fully with reference to the accompanying drawings, in which example embodiments are shown. However, the invention should not be construed as limited to the embodiments set forth herein. Disclosed features of example embodiments may be combined as readily understood by one of ordinary skill in the art to which this invention belongs. Like numbers refer to like elements throughout. Well-known functions or constructions will not necessarily be described in detail for brevity and/or clarity.

Figure 1:
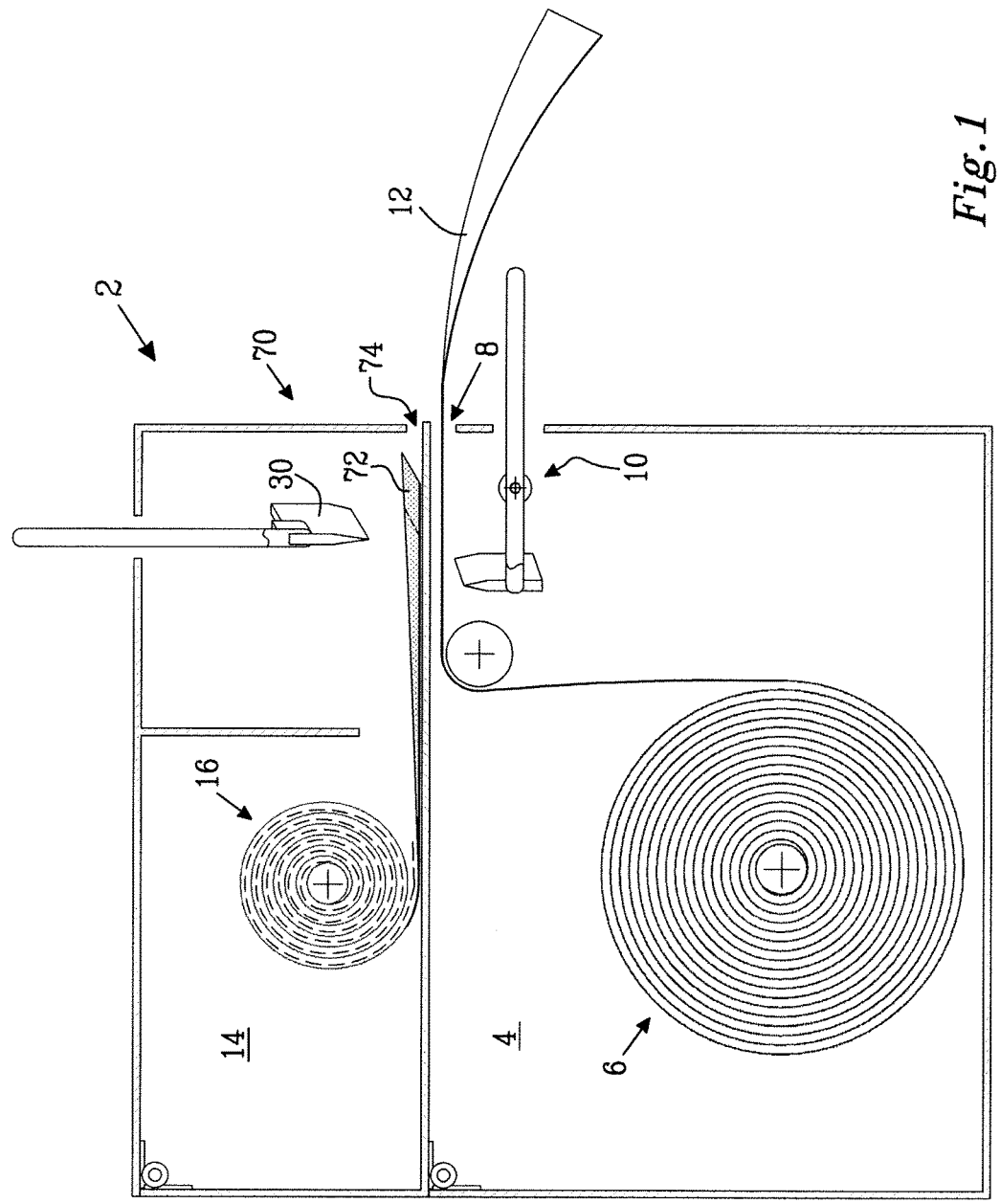
FIG. 1 illustrates a cross section through a dispenser according to some embodiments.

FIG. 1 illustrates a cross section through a dispenser 2 according to some embodiments. The dispenser 2 is adapted for on-demand dispensing of a length of belt material and a first hook material patch for use with an absorbent product. The dispenser 2 includes a first holder 4 for a roll 6 of continuous belt material, a dispensing outlet 8 for the belt material, a separating element 10 for separating a length of belt material 12 from the roll 6 of continuous belt material, a second holder 14 for a roll 16 of continuous web of hook material, and a hook material patch providing device 70. The hook material patch providing device 70 is arranged to cooperate with the second holder 14 for dispensing the first hook material patch.

The dispenser 2 is adapted to dispense one length of belt material at a time. The first holder 4 is adapted to hold a roll 6 of continuous belt material having a width corresponding to a width of the belts being dispensed from the dispensing outlet 8. The hook material patch providing device 70 includes a cutting element 30. The cutting element 30 is movable towards an end portion 72 of the continuous web of hook material to cut the first hook material patch from the roll 16 of continuous web of hook material. The first hook material patch is dispensed from a dispensing opening 74 of the dispenser 2. The dispensing opening 74 may be a separate opening or it may form one opening in the dispenser 2 together with the dispensing outlet 8.

The separating element 10 includes a cutting edge 20. The length of belt material is separated from the continuous belt material by means of the separating element 10 when the cutting edge 20 is moved against the continuous belt material.

From the dispenser 2, either a length of belt material 12, or a first hook material patch may be dispensed. Furthermore, if both a length of belt material 12 and a first hook material patch are dispensed, the first hook material patch may be deposited onto the length of belt material to thus, form a belt for use with an absorbent product.

Figure 2:
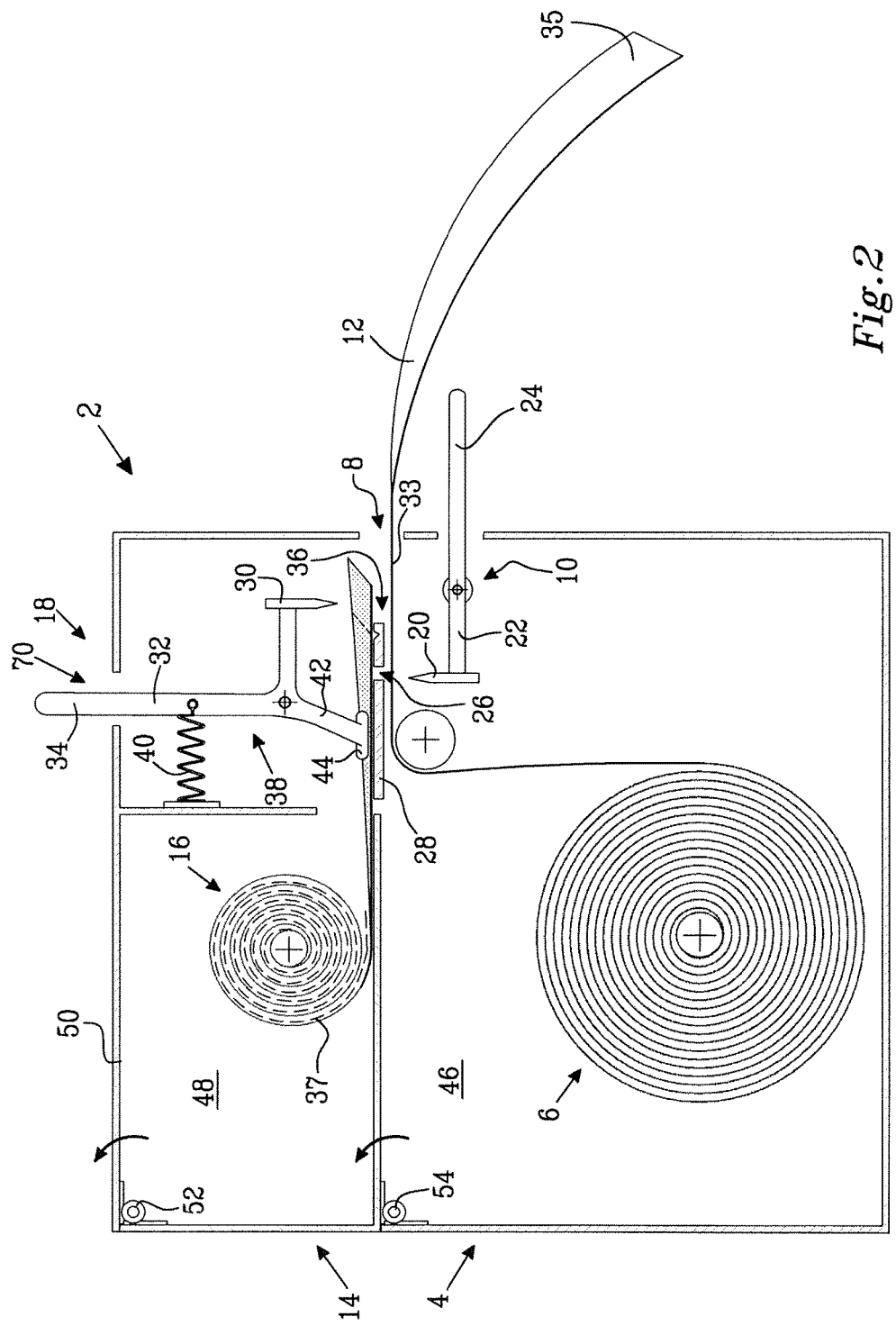
FIG. 2 illustrates a cross section through another dispenser according to some embodiments.

FIG. 2 illustrates a cross section through a dispenser 2 according to some embodiments. The dispenser 2 is adapted for on-demand dispensing of a belt for use with an absorbent product. The dispenser 2 includes a first holder 4 for a roll 6 of continuous belt material, a dispensing outlet 8 for the belt material, a separating element 10 for separating a length of belt material 12 from the roll 6 of continuous belt material, and a second holder 14 for a roll 16 of continuous web of hook material. A hook material patch providing device 70 includes a depositing arrangement 18 is arranged for depositing a first hook material patch onto the length of belt material 12, to thereby form the belt. The dispenser 2 is adapted to dispense one belt at a time. The first holder 4 is adapted to hold a roll 6 of continuous belt material having a width corresponding to a width of the belts being dispensed from the dispensing outlet 8.

The separating element 10 includes a cutting edge 20 connected to a first lever 22. The first lever 22 is pivotably attached to the dispenser 2. A user operates a handle end 24 of the first lever 22 to pivot the first lever 22 and to displace the cutting edge 20 into a cutting slot 26 provided in a contact plate 28. The continuous belt material abuts against the contact plate 28 and the length of belt material 12 is separated from the continuous belt material as it is sheared between the cutting edge 20 and the contact plate 28. The dispenser 2 may be provided with an arrangement (not shown) for advancing a tail of the continuous belt material of the roll 6 towards the dispensing outlet 8, for a user to grasp and pull on for dispensing a next length of belt material.

The depositing arrangement 18 includes a cutting element 30 for separating the first hook material patch from the roll 16 of the continuous web of hook material. The continuous web of hook material abuts against the contact plate 28 on a side opposite to the continuous belt material. The cutting element 30 is connected to a lever arrangement 32. A user operates a handle portion 34 of the lever arrangement 32 to pivot the lever arrangement 32 and to displace the cutting element 30 towards, and past, an edge 36 of the contact plate 28. The first hook material patch is thus separated from the continuous web of hook material as the continuous web of hook material is sheared between the cutting element 30 and the contact plate 28.

The cutting element 30 and the edge 36 are located downstream of the cutting edge 20 and the cutting slot 26. Thus, the first hook material patch is deposited onto the length of belt material 12 a bit from an end of the length of belt material 12. Put differently, the length of belt material 12 has a first end portion 33 and a second end portion 35, and the first hook material patch is deposited onto the belt in the first end portion 33. The hook material may be provided with a hook surface structure on both of its sides and the belt material may have a loop surface structure. Hooks on a first side of the first hook material patch, closest to the belt material, may thus engage with the length of belt material. A separation sheet 37, made from e.g., paper, may be provided between the coils of continuous web of hook material in the roll 16 of continuous web of hook material to prevent the hooks of the two sides of the continuous web of hook material from engaging with each other.

The dispenser 2 includes a feeding arrangement 38 for feeding the continuous web of hook material in a direction from the second holder 14 towards the cutting element 30. The feeding arrangement 38 forms part of the lever arrangement 32 and may include a return spring 40 and an abutment part 42 having a resilient end 44. After a user has pulled on the handle portion 34 to separate the first hook material patch by means of the cutting element from the continuous web of hook material, the lever arrangement 32 may be returned to its initial position by means of the return spring 40. Alternatively, the return spring 40 may be omitted and the lever arrangement 32 may be manually returned to its initial position by a user of the dispenser 2. Upon returning to its initial position, the resilient end of the abutment part engages with the continuous web of hook material and slides it along the contact plate 28, such that a portion of the continuous web of hook material extends outside the edge 36. Thus, a new hook material patch is ready to be separated from the continuous web of hook material by the cutting element 30 when a new belt is to be dispensed. The dispenser 2 may be provided with a holding arrangement (not shown) for holding the continuous web of hook material in place against the contact plate 28 as a user pulls on the handle portion 34.

The dispenser 2 includes a first compartment 46 including the first holder 4 and a second compartment 48 including the second holder 14. The first compartment 46 may be opened independently of the second compartment 48. The second compartment 48 may be opened independently of the first compartment 46. The dispenser 2 may thus be separately replenished with continuous belt material and continuous web of hook material. Access to the second compartment 48 may be provided by means of a lid 50 being pivotably attached at a top end of the dispenser 2 by means of a first hinge 52. Access to the first compartment 46 may be provided by means of an upper portion of the dispenser 2 being pivotably attached to a wall section of the dispenser 2 by means of a second hinge 54.

Also with the dispenser 2 according to these embodiments, it is possible to dispense only a length of belt material 12, or only a first hook material patch.

FIG. 3 illustrates a partial cross section through a dispenser 2 according to embodiments. The dispenser 2 is adapted for on-demand dispensing of a belt for use with an absorbent product. The dispenser 2 includes a first holder 4 for a stack 56 of folded continuous belt material, a dispensing outlet 8 for the belt material, a separating element 10 for separating a length of belt material 12 from the stack 56 of continuous belt material. The dispenser 2 further includes a second holder 14 for stack of pre-cut hook material patches, and hook material patch providing device 70 including a depositing arrangement 18 arranged for depositing a first hook material patch 57 onto the length of belt material 12, to thereby form the belt. The dispenser 2 is adapted to dispense one belt at a time.

The depositing arrangement 18 includes a feeding member 58 arranged to feed the first hook material patch 57 from the stack of pre-cut hook material patches in the second holder 14 onto the length of belt material 12. The second holder 14 includes a feeding tube 60 inside which the pre-cut hook material patches of the stack of pre-cut hook material patches are supported. At a lower end of the feeding tube 60 there is provided a feeding slot 64, through which the feeding member 58 is arranged to eject the first hook material patch 57 from the stack of pre-cut hook material patches and the second holder 14 to deposit it onto the length of belt material 12.

The depositing arrangement 18 further includes a gluing arrangement 62. A droplet or bead of glue is ejected from the gluing arrangement 62 to fasten the first hook material patch 57 on the length of belt material 12.

A user may activate the gluing arrangement 62 prior to operating the feeding member 58 to deposit the first hook material patch onto the length of belt material 12. Thereafter, the user may initiate the separating element 10 to separate the length of belt material 12 from the stack 56 of continuous belt material, to thereby form the belt.

The dispenser 2 includes a measuring device 66, in the form of a ruler, arranged for measuring the length of belt material 12.

FIG. 4 illustrates a belt 68 according to some embodiments adapted for use with an absorbent product. The belt 68 includes a length of belt material 12 and a hook material patch 57. For illustration purposes, the hook material patch 57 is illustrated only partially attached to the length of belt material 12. Both sides of the length of belt material 12 have a loop surface structure adapted to engage with a hook structure of the hook material patch 57. The belt material may for instance be a textile, a textile-like material, a woven material, or a nonwoven material.

The hook material of the hook material patch 57 has two sides. Each of the two sides is provided with a hook surface structure. The hook surface structures of the two sides may have different properties. For instance, the hook surface structure of the side engaging with the belt in the illustrated open position of the belt 68 may have stronger engaging properties than the side facing away from the belt 68. In this manner, it may be ensured that the hook material patch 57 remains attached to the belt 68 in the same position of the length of belt material 12 also after the belt 68 has been closed and opened one or more times.

Figure 5:
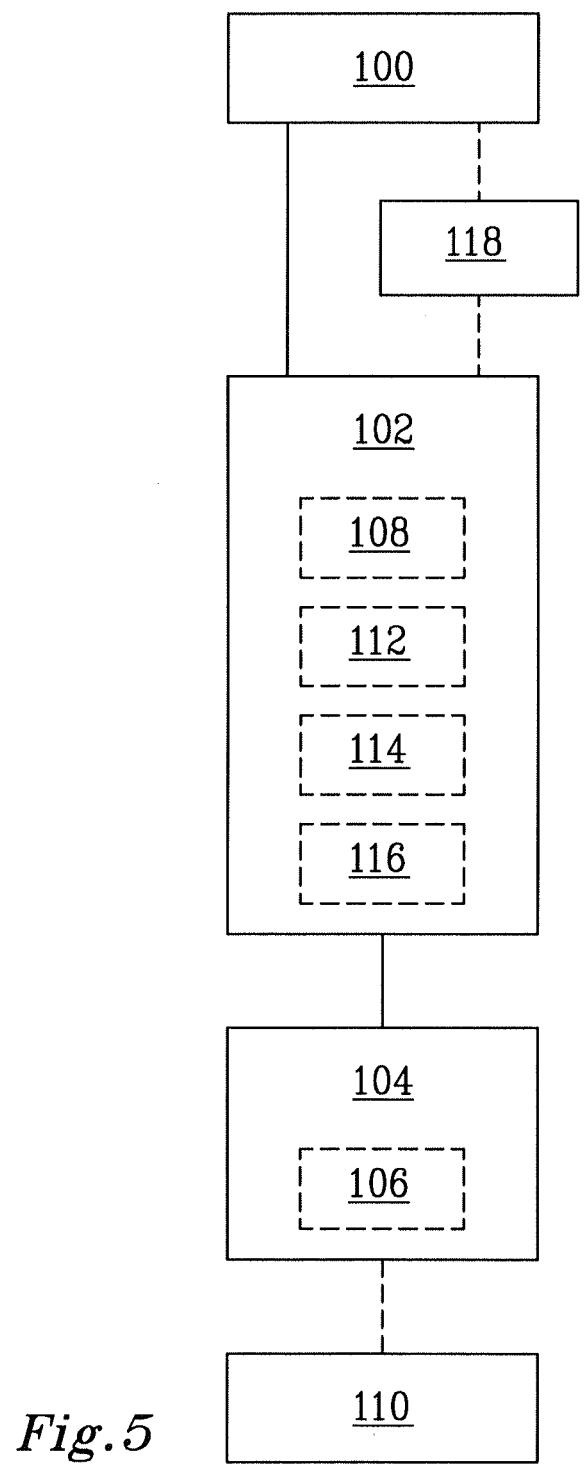
FIG. 5 illustrates a flow chart illustrating a method of on-demand dispensing a belt for use with an absorbent product.

FIG. 5 illustrates a method of on-demand dispensing a belt for use with an absorbent product. The dispenser includes a first holder holding a roll or a stack of continuous belt material, a dispensing outlet for the belt material, a separating element for separating a length of belt material from the roll or the stack of continuous belt material, a second holder holding at least a first hook material patch, and a depositing arrangement arranged for depositing the first hook material patch onto the length of belt material. The dispenser may for instance be a dispenser 2 in accordance with the embodiments illustrated and described in connection with FIGS. 2 and 3. The method includes:

extracting 100 a length of belt material from the roll or the stack of continuous belt material via the dispensing outlet, depositing 102 the first hook material patch onto the length of belt material utilizing the depositing arrangement, and separating 104 the length of belt material from the roll or stack of continuous belt material to thereby form the belt.

According to certain embodiments, the separating 104 may include: cutting 106 the belt from the roll or the stack of continuous belt material at a desired length.

According to certain embodiments, the length of belt material may have a first end portion and a second end portion, wherein the depositing 102 may include: positioning 108 the first hook material patch onto the belt in the first end portion or in the second end portion.

According to certain embodiments, the depositing 102 may be performed before the separating 104.

According to certain embodiments, the second holder may hold a stack or a roll of a continuous web of hook material and the depositing arrangement may include a cutting element for separating the first hook material patch from the roll or the stack of the continuous web of hook material, wherein the dispenser may include a feeding arrangement for feeding the continuous web of hook material in a direction from the second holder towards the cutting element. The method further may include:

feeding 110 the continuous web of hook material in the direction from the second holder towards the cutting element, and the depositing 102 may include:

cutting 112 the first hook material patch from the roll or the stack of the continuous web of hook material.

According to certain embodiments, the second holder may hold a stack of pre-cut hook material patches, the stack of pre-cut hook material patches including the first hook material patch, wherein the depositing arrangement may include a feeding member arranged to feed the first hook material patch onto the length of belt material. The depositing 102 may include:

feeding 114 the first hook material patch onto the length of belt material.

According to certain embodiments, the roll or stack of continuous belt material may include a belt material having a loop surface structure and the hook material of the first hook material patch has two sides, each of the two sides being provided with a hook surface structure. The depositing 102 may include:

engaging 116 the first hook material patch with the belt material in a hook and loop connection.

According to certain embodiments, the method may include: measuring 118 the length of belt material.

The belt 68 illustrated in FIG. 4 may be dispensed in accordance with the method discussed in connection with FIG. 5. For example, the belt 68 may be dispensed utilizing the steps of: extracting 100, depositing 102, and separating 104, wherein the depositing 102 includes the step of: engaging 116 the first hook material patch with the belt material in a hook and loop connection.

Example embodiments described above may be combined as understood by a person skilled in the art. For instance, the dispenser 2 according to embodiments disclosed in FIGS. 1 and 2 may include a hook material patch providing device including a depositing arrangement for pre-cut hook material patches according to the embodiments disclosed in FIG. 3 instead of a depositing arrangement including a cutting element. Conversely, the dispenser 2 according to embodiments disclosed in FIG. 3 may include a hook material patch providing device including a depositing arrangement including a cutting element according to the embodiments disclosed in FIG. 1 or 2 instead of a depositing arrangement for pre-cut hook material patches. Similarly, the hook material patches of the FIG. 2 embodiments may be glued to the length of belt material in the depositing, and the hook material patches of the FIG. 3 embodiments may be attached to the length of belt material by a hook and loop engagement in the depositing. It is also understood by those skilled in the art that one or more of the individual operations/steps required for dispensing a belt from the dispenser 2 may be performed manually, for example by means of levers which require manual power to be operated (as disclosed in connection with FIG. 2), or one or more of the individual operations/steps required for dispensing a belt from the dispenser 2 may be electrically powered, in which case electric motors and/or actuators may be utilized. In both cases, using either manual or electric power, it is a user who dispenses a belt on-demand.

In addition to the example embodiments described above, many different alterations, modifications and the like will become apparent for those skilled in the art. For instance, instead of the first lever 22 and/or the lever arrangement 32 a respective knob or wheel for a user to grasp may be provided. Furthermore, only one manual actuator, such as a lever, knob, or wheel, may be provided in the dispenser for actuating both the separating element and the hook material patch providing device. The first hook material patch may be attached to the length of belt material by other means than the described hook and loop mechanical fastening or gluing. For instance, the first hook material patch may be welded or heat bonded to the length of belt material. Heat may be provided by an electrically heated element or an ultrasonic welding/bonding arrangement in the dispenser.

Therefore, it is to be understood that the foregoing is illustrative of various example embodiments and that the invention is defined only by the appended claims.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. A dispenser for on-demand dispensing of a length of belt material and a first hook material patch, the length of belt material and the first hook material patch is used with an absorbent product, comprising:
   a first holder to hold a roll or a stack of continuous belt material,
   a first dispensing outlet to dispense the belt material disposed on the exterior of the dispenser,
   a separating element that separates the length of belt material from the roll or the stack of continuous belt material,
   a second holder to hold at least the first hook material patch,
   a second dispensing outlet to dispense the first hook material patch dispensed on the exterior of the dispenser, and
   a hook material patch providing device, wherein the hook material patch providing device in combination with the second holder dispenses the first hook material patch through the second dispensing outlet, and
   wherein the hook material patch providing device comprises a cutter that separates the first hook material patch from a roll or a stack of a continuous web of hook material held in the second holder, or wherein the hook material patch providing device comprises a feeder that feeds the first hook material patch from a stack of pre-cut material patches held in the second holder.

2. The dispenser according to claim 1, wherein the dispenser dispenses one length of belt material at a time, wherein a length of belt material dispensed through the dispensing outlet has a belt width, and wherein the first holder is adapted to hold a roll or a stack of continuous belt material having a width corresponding to the belt width.

3. The dispenser according to claim 1, wherein the dispenser is used with a belt material having a loop surface structure.

4. The dispenser according to claim 1, wherein the hook material of the first hook material patch has two sides, each of the two sides being provided with a hook surface structure.

5. The dispenser according to claim 1, wherein the dispenser comprises a first compartment comprising the first holder, and a second compartment comprising the second holder, and wherein the first compartment and the second compartment are separately openable for replenishing the dispenser with continuous belt material and hook material.

6. The dispenser according to claim 1, further comprising a measuring device arranged for measuring the length of belt material.

* * * * *